United States Patent
Meyer et al.

(10) Patent No.: US 6,861,390 B2
(45) Date of Patent: Mar. 1, 2005

(54) DERIVATIVES OF UK-2A

(75) Inventors: Kevin Gerald Meyer, Zionsville, IN (US); Richard Brewer Rogers, Mobile, AL (US); Noormohamed Mohamed Niyaz, Indianapolis, IN (US); Jenifer Lynn Adamski Butz, Avon, IN (US); Bassam Salim Nader, Fishers, IN (US); Chenglin Yao, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/493,456

(22) PCT Filed: Oct. 23, 2002

(86) PCT No.: PCT/US02/33947

§ 371 (c)(1),
(2), (4) Date: Apr. 23, 2004

(87) PCT Pub. No.: WO03/035617

PCT Pub. Date: May 1, 2003

(65) Prior Publication Data

US 2004/0192924 A1 Sep. 30, 2004

Related U.S. Application Data

(60) Provisional application No. 60/335,814, filed on Oct. 23, 2001.

(51) Int. Cl.$^7$ .............................................. A01N 43/40

(52) U.S. Cl. .................................... 504/251; 546/281.7

(58) Field of Search ........................ 504/251; 514/336; 546/281.7

(56) References Cited

PUBLICATIONS

Ueki, M., et al., "UK–2A, B, C and D Noveml Antifungal Antibiotics from *Streptomyces* sp. 517–02" Journal of Antibiotics vol. 49, No. 7 p. 639–643 (1996).

*Primary Examiner*—Amelia A. Owens
(74) *Attorney, Agent, or Firm*—Lynn M. Zettler; Carl D. Corvin

(57) ABSTRACT

Derivatives of UK-2A are provided.

5 Claims, No Drawings

DERIVATIVES OF UK-2A

This application claims the benefit or Provisional Application 60/335,814 filed on Oct. 23, 2001.

FIELD OF THE INVENTION

This invention is related to the field of compounds that are derivatives of UK-2A.

BACKGROUND OF THE INVENTION

UK-2A is a natural product having the following formula.

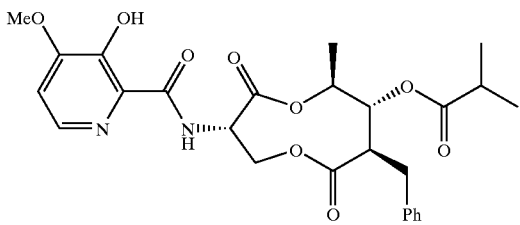

UK-2A is described in M. Ueki, et al. *J. Antibiot.* 1996, 49, 639. While this compound has certain properties that make it useful in a variety of fields, currently, it is being investigated as a starting point for making compounds that have efficacy in the fungicide area.

DETAILED DESCRIPTION OF THE INVENTION

As used herein, the terms alkyl, alkoxy, alkenyl, and alkynyl shall include both branched and unbranched carbon atom chains.

As used herein, the terms alkenyl, alkynyl, and cycloalkenyl shall contain one or more unsaturated carbon-carbon bonds.

As used herein, the term cycloalkyl shall mean a 3 to 8 membered saturated ring containing 0–2 heteroatoms selected from the group consisting of O, N, and S.

As used herein, the term "aryl" shall mean phenyl or naphthyl.

As used herein, the term "heteroaryl" shall mean any 5 or 6 membered aromatic ring, containing one or more heteroatoms, where such heteroatoms are selected from the group consisting of O, N, and S, and where the remaining atoms of the aromatic ring are carbon atoms. Suitable examples include, but are not limited to pyridine, pyridazine, pyrimidine, pyrazine, pyrrole, pyrazole, imidazole, furan, thiophene, oxazole, isoxazole, thiazole, isothiazole, quinoline, quinoxoline and thiadiazole.

As used herein, the term:

"Me" shall mean methyl ($CH_3$);
"Et" shall mean ethyl ($CH_2CH_3$);
"Pr" shall mean propyl ($CH_2CH_2CH_3$);
"Bu" shall mean butyl ($CH_2CH_2CH_2CH_3$);
"Ph" shall mean phenyl ($C_6H_5$);
"ppm" shall mean parts per million;
"psi" shall mean pounds per square inch;
"m.p." shall mean the melting point;
"b.p." shall mean the boiling point;
"RT" shall mean ambient room temperature;
"IG" shall mean a gas that is substantially inert under the reaction conditions disclosed herein, suitable examples are argon, nitrogen, and helium;
"DMS" shall mean dimethylsulfide;
"DME" shall mean 1,2-dimethoxyethane;
"DMF" shall mean N,N-dimethylformamide;
"TMSBr" shall mean bromotrimethylsilane;
"EtOAc" shall mean ethyl acetate; and
"DMSO" shall mean dimethylsulfoxide.

As used herein, the term "disease inhibiting and phytologically acceptable amount", refers to an amount of a compound of the present Invention which kills or inhibits the plant pathogen and prevents, eradicates, or arrests plant disease for which control is desired, but is not significantly toxic to the plant. This amount will generally be from about 0.1 to 1000 ppm, with 10 to 500 ppm being preferred. The exact concentration of compound required varies with the fungal disease to be controlled, the type of formulation employed, the method of application, the particular plant species, climate conditions, and other factors. A suitable application rate is typically in the range from about 10 to about 1000 grams per hectare (g/Ha).

Throughout this document, all temperatures are given in degrees Celsius (° C.) and all percentages are weight percentages, unless otherwise stated.

The compounds of the invention are described by Formula One:

Formula One

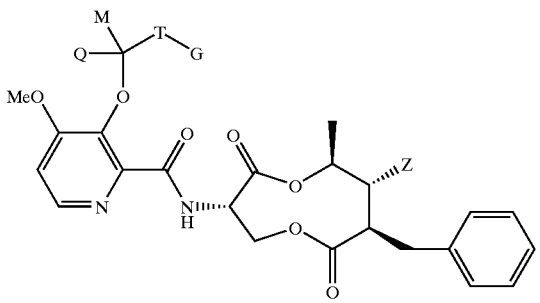

wherein:

Z is selected from the group consisting of H, $R^{11}$, $OR^{11}$, $OC(O)R^{11}$, $OC(O)OR^{11}$, and $OC(O)NR^{11}R^{12}$, $OC(O)NR^{11-12}R^{12-11}$;

$R^{11}$ is selected from the group consisting of $C_1$–$C_8$ alkyl, $C_2$–$C_8$ alkenyl, $C_2$–$C_8$ alkynyl, $C_3$–$C_8$ cycloalkyl, aryl, and heteroaryl;

$R^{12}$ is selected from the group consisting of H, $C_1$–$C_6$ alkyl, $C_3$–$C_6$ cycloalkyl, $C_2$–$C_5$ alkenyl, and $C_2$–$C_5$ alkynyl;

$NR^{11-12}R^{12-11}$ is a 5 to 8 membered ring, where the members of the ring are selected from the group consisting of C, O, and S Q is selected from the group consisting of H, $CH_3$, $CH_2CH_3$, $CF_3$, Ph, $CH=CH_2$, and cyclopropyl;

M is selected from the group consisting of H, $CH_3$, $CH_2CH_3$, $CF_3$, Ph, $CH=CH_2$, or cyclopropyl;

T is selected from the group consisting of O, OC(O), OC(O)O, S, SC(O), SC(O)O, or

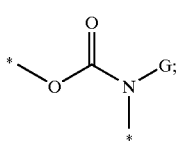

G is selected from the group consisting of H, $C_1$–$C_6$ alkyl, $C_2$–$C_6$ alkenyl, $C_2$–$C_6$ alkynyl, $C_3$–$C_6$ cycloalkyl, aryl, and heteroaryl; optionally, G and M may form a 3–8 membered carbocyclic system; optionally, M and Q may form a 3–8 membered carbocyclic system; wherein each of the alkyl, alkoxy, alkenyl, alkynyl, cycloalkyl, cycloalkenyl, benzyl, aryl, and heteroaryl may be substituted with one or more substituents.

The substituents can be any substituent that does not substantially interfere with the fungicidal properties of the compound when compared to UK-2A. In the following examples of substituents a "–" after the name indicates the point of attachment.

Examples of the substituents include, but are not limited to, the group consisting of $C_1$–$C_6$ alkyl-, $C_2$–$C_6$ alkenyl-, $C_2$–$C_6$ alkynyl-, $C_3$–$C_6$ cycloalkyl-, $C_5$–$C_6$ cycloalkenyl-, aryl-, heteroaryl-, halo-, nitro-, hydroxy-, cyano-, $C_1$–$C_6$ alkoxy-, $C_2$–$C_6$ alkenoxy-, $C_3$–$C_6$ cycloalkoxy-, aryloxy-, heteroaryloxy-, acyloxy-, $C_1$–$C_6$ alkylacyloxy-, $C_3$–$C_6$ cycloalkylacyloxy-, arylacyloxy-, heteroarylacyloxy-, $C_1$–$C_6$ alkyloxyacyl-, $C_3$–$C_6$ cycloalkyloxyacyl-, aryloxyacyl-, heteroaryloxyacyl-, $C_1$–$C_6$ alkylacyl-, $C_3$–$C_6$ cycloalkylacyl-, arylacyl-, heteroarylacyl-, $C_1$–$C_6$ alkylacylamino-, $C_3$–$C_6$ cycloalkylacylamino-, arylacylamino-, heteroarylacylamino-, $C_1$–$C_6$ alkylaminoacyl-, $C_3$–$C_6$ cycloalkylaminoacyl-, arylaminoacyl-, heteroarylaminoacyl-, $C_1$–$C_6$ alkylthio-, $C_3$–$C_6$ cycloalkylthio-, arylthio-, heteroarylthio-, $C_1$–$C_6$ alkylsulfonyl-, $C_3$–$C_6$ cycloalkylsulfonyl-, arylsulfonyl-, heteroarylsulfonyl-, $C_1$–$C_6$ alkylsulfinyl-, $C_3$–$C_6$ cycloalkylsulfinyl-, arylsulfinyl-, heteroarylsulfinyl-, —C(NOR$^X$)R$^Y$ where R$^Y$ and R$^X$ are independently H—, $C_1$–$C_6$ alkyl-, $C_2$–$C_6$ alkenyl-, $C_3$–$C_6$ cycloalkyl-, aryl- or heteroaryl—in which any alkyl or cycloalkyl containing substituent may be substituted with one or more halogens.

These substituents may also be substituted with substituents selected from group consisting of $C_{1-6}$ alkyl-, $C_2$–$C_6$ alkenyl-, $C_2$–$C_6$ alkynyl-, $C_3$–$C_6$ cycloalkyl-, $C_5$–$C_6$ cycloalkenyl-, aryl-, heteroaryl-, halo-, nitro-, hydroxy-, cyano-, $C_1$–$C_6$ alkoxy-, $C_2$–$C_6$ alkenoxy-, $C_3$–$C_6$ cycloalkoxy-, aryloxy-, heteroaryloxy-, acyloxy-, $C_1$–$C_6$ alkylacyloxy-, $C_3$–$C_6$ cycloalkylacyloxy-, arylacyloxy-, heteroarylacyloxy-, $C_1$–$C_6$ alkyloxyacyl-, $C_3$–$C_6$ cycloalkyloxyacyl-, aryloxyacyl-, heteroaryloxyacyl-, $C_1$–$C_6$ alkylacyl-, $C_3$–$C_6$ cycloalkylacyl-, arylacyl-, heteroarylacyl-, $C_1$–$C_6$ alkylacylamino-, $C_3$–$C_6$ cycloalkylacylamino-, arylacylamino-, heteroarylacylamino-, $C_1$–$C_6$ alkylaminoacyl-, $C_3$–$C_6$ cycloalkylaminoacyl-, arylaminoacyl-, heteroarylaminoacyl-, $C_1$–$C_6$ alkylthio-, $C_3$–$C_6$ cycloalkylthio-, arylthio-, heteroarylthio-, $C_1$–$C_6$ alkylsulfonyl-, $C_3$–$C_6$ cycloalkylsulfonyl-, arylsulfonyl-, heteroarylsulfonyl-, $C_1$–$C_6$ alkylsulfinyl-, $C_3$–$C_6$ cycloalkylsulfinyl-, arylsulfinyl-, heteroarylsulfinyl-, —C(NOR$^X$)R$^Y$ where R$^Y$ and R$^X$ are independently H—, $C_{1-6}$ alkyl-, $C_2$–$C_6$ alkenyl-, $C_3$–$C_6$ cycloalkyl-, aryl- or heteroaryl—in which any alkyl or cycloalkyl containing substituent may be substituted with one or more halogens.

Specific examples of substituents are (mono or poly, chloro or fluoro) alkyl, benzyl, and benzyloxy.

Sometimes it is desirable to use heteroaryl or aryl substituents that are fused together with other aryl or heteroaryl substituents.

Various hydrates and complexes of compounds of Formula One can be made in the conventional ways.

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion. The compounds of the invention may also be used to protect stored grain and other non-plant loci from fungal infestation.

The compounds of this invention are preferably applied in the form of a composition comprising one or more of the inventive compounds with a phytologically-acceptable carrier. These compositions are either concentrated formulations which are dispersed in water, or another liquid for application, or are dust or granular formulations, which are applied without further treatment.

The compositions are prepared according to procedures which are conventional in the agricultural chemical art, but which are novel and important because of the presence therein of the compounds of this invention. Some description of the formulation of the compositions is given to assure that agricultural scientists can readily prepare desired compositions.

The dispersions in which the compounds are applied are most often aqueous suspensions, or emulsions, prepared from concentrated formulations of the compounds. Such water-soluble, water suspendable, or emulsifiable, formulations are either solids, usually known as wettable powders, or liquids, usually known as emulsifiable concentrates, or aqueous suspensions. The present invention contemplates all vehicles by which the compounds of this invention can be formulated for delivery for use as a fungicide. As will be readily appreciated, any material to which these compounds can be added may be used, provided they yield the desired utility without significant interference with activity of the compounds of this invention as antifungal agents.

Wettable powders, which may be compacted to form water dispersible granules, comprise an intimate mixture of the active compound, an inert carrier, and surfactants. The concentration of the active compound is usually from about 10% to about 90% w/w, more preferably about 25% to about 75% w/w. In the preparation of wettable powder compositions, the active compounds can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground, or mixed, with the active compound in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants such as ethylene oxide adducts of alkyl phenols.

Emulsifiable concentrates of the compounds of this invention comprise a convenient concentration, such as from about 10% to about 50% w/w, in a suitable liquid. The compounds are dissolved in an inert carrier, which is either a water miscible solvent, or a mixture of water-immiscible organic solvents and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used such as, for example, terpenic solvents including rosin derivatives, aliphatic ketones, such as cyclohexanone, and complex alcohols such as 2-ethoxyethanol.

Emulsifiers which can be advantageously employed herein can be readily determined by those skilled in the art and include various nonionic, anionic, cationic, and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines, or fatty acids with ethylene oxide, propylene oxides such as the ethoxylated alkyl phenols, and carboxylic esters solubilized with polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulphated polyglycol ethers, and appropriate salts of phosphated polyglycol ether.

Representative organic liquids which can be employed in preparing the emulsifiable concentrates of the present invention are the aromatic liquids such as xylene, propyl benzene fractions or mixed naphthalene fractions, mineral oils, substituted aromatic organic liquids such as dioctyl phthalate, kerosene, and dialkyl amides of various fatty acids; particularly the dimethyl amides of fatty glycols and glycol derivatives such as the n-butyl ether, ethyl ether, or methyl ether of diethylene glycol, and the methyl ether of triethylene glycol. Mixtures of two or more organic liquids are also often suitably employed in the preparation of the emulsifiable concentrate. The preferred organic liquids are xylene and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of this invention, dispersed in an aqueous vehicle at a concentration in the range from about 5% to about 50% w/w. Suspensions are prepared by finely grinding the compound and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

Granular compositions usually contain from about 0.5% to about 10% w/w of the compound dispersed in an inert carrier which consists entirely or in large part of coarsely divided attapulgite, bentonite, diatomite, clay, or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated by making a dough or paste of the carrier and compound, and crushing, and drying to obtain the desired granular particle Dusts containing the compounds are prepared simply by intimately mixing the compound in powdered form with a suitable dusty agricultural carrier such as, for example, kaolin clay, ground volcanic rock, and the like. Dusts can suitably contain from about 1% to about 10% w/w of the compound.

The active compositions may contain adjuvant surfactants to enhance deposition, wetting, and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines, and blends of surfactants with mineral or vegetable oils.

The composition may optionally include fungicidal combinations which comprise at least 1% of one or more of the compounds of this invention with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds in combination can generally be present in a ratio of from 1:100 to 100:1

The present invention includes within its scope methods for the control or prevention of fungal attack. These methods comprise applying to the locus of the fungus, or to a locus in which the infestation is to be prevented (for example applying to cereal), a fungicidal amount of one or more of the compounds of this invention or compositions. The compounds are suitable for treatment of various plants at fungicidal levels while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds, or foliage of plants for the control of various fungi without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect, particularly for agricultural use. Many of the compounds are particularly effective for use with agricultural crops and horticultural plants, or with wood, paint, leather, or carpet backing.

In particular, the compounds effectively control a variety of undesirable fungi which infect useful plant crops. Activity has been demonstrated for a variety of fungi, including, for example, the following representative fungi species: Apple Scab (*Venturia inaequalis*—VENTIN), Brown Rust of Wheat (*Puccinia recondita*—PUCCRT), Stripe Rust of Wheat (*Puccinia striiformis*—PUCCST), Rice Blast (*Pyricularia oryzae*—PYRIOR), Leaf Spot of Beet (*Cercospora beticola*—CERCBE), Powdery Mildew of Wheat (*Etysiphe graminis*—ERYSGT), Leaf Blotch of Wheat (*Septoria tritici*—SEPTTR), Eyespot of Wheat (*Pseudocercosporella herpotrichoides*—PSDCHE), Brown Rot of Peach (*Monilinia fructicola*—MONIFC), and Glume Blotch of Wheat (*Leptosphaeria nodorum*—LEPTNO). It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the compounds of this invention and compositions containing the same, may not be equally effective at similar concentrations or against the same fungal species. The compounds of this invention and compositions are effective in use with plants in a disease inhibiting and phytologically acceptable amount.

EXAMPLES

These examples are provided to further illustrate the invention, but are not meant to limit the invention to these specific examples.

Picolinamide natural product UK-2A (1a) and the generation of compounds 2a–f are described in M. Ueki, et al. *J. Antibiot.* 1996, 49, 639 and WO 01/14339 A2 2001, respectively. Compound 2g was synthesized via diol 1b (vide infra). Acyl- and alkoxymethyl ethers and thioalkoxymethyl ethers of 1a and derivatives (2a–2g) are prepared by capping the 3-hydroxy moiety of the substituted picolinamide with the appropriate halogen substituted electrophile using standard reaction conditions (eq. 1).

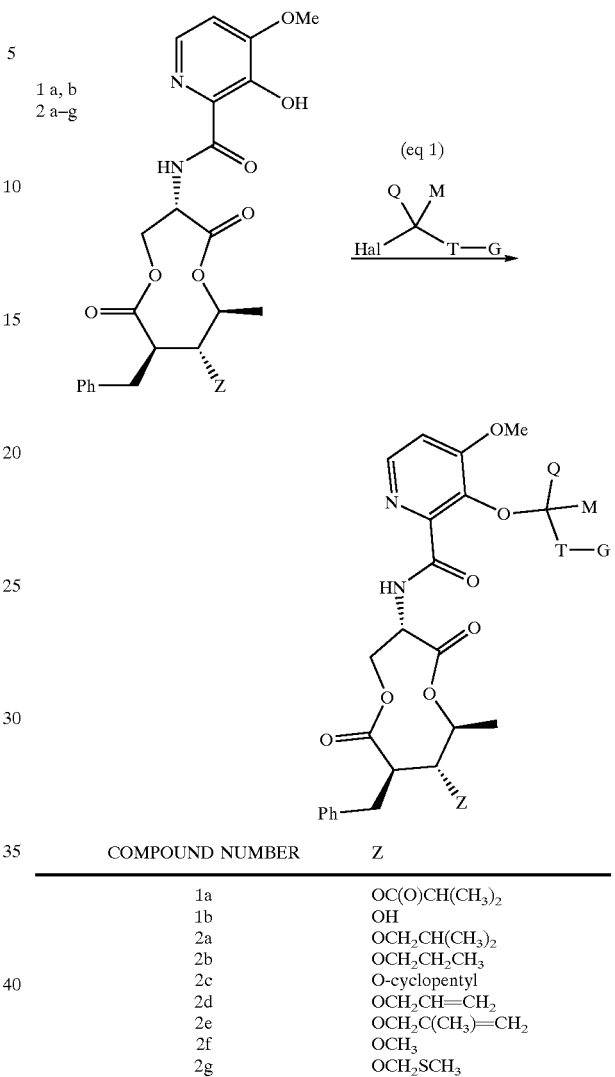

| COMPOUND NUMBER | Z |
|---|---|
| 1a | OC(O)CH(CH$_3$)$_2$ |
| 1b | OH |
| 2a | OCH$_2$CH(CH$_3$)$_2$ |
| 2b | OCH$_2$CH$_2$CH$_3$ |
| 2c | O-cyclopentyl |
| 2d | OCH$_2$CH=CH$_2$ |
| 2e | OCH$_2$C(CH$_3$)=CH$_2$ |
| 2f | OCH$_3$ |
| 2g | OCH$_2$SCH$_3$ |

N-[(3S,7R,8R,9S)-7-benzyl-8-hydroxy-9-methyl-2,6-dioxo-1,5-dioxonan-3-yl]-3-hydroxy-4-methoxypyridine-2-carboxamide (1b)

Diisobutylaluminum hydride (1.5 M in toluene, 7.85 mmol) was added slowly to a 5° C. suspension of 1a (1.94 mmol, 1.0 g) in toluene (10 mL). The addition was monitored so as to maintain the reaction temperature below 20° C. The mixture was stirred an additional 15 min and quenched with EtOAc (45 mL). Hydrochloric acid (2N, 100 mL) was added slowly and stirred vigorously for 15 min. The layers were separated and the organic layer dried (MgSO$_4$) and concentrated in vacuo to give 656 mg (76%) of a foamy, light yellow solid. $^1$H-NMR data was consistent with the title compound. Exact Mass: m/z calcd. for C$_{22}$H$_{24}$N$_2$O$_8$ [M]$^+$=444.1533, found 444.1513.

N-{(3S,7R,8R,9S)-7-benzyl-9-methyl-8-[(methylthio)methoxy]-2,6-dioxo-1,5-dioxonan-3-yl}-3-hydroxy-4-methoxypyridine-2-carboxamide (2g)

Compound 1b (2.0 g, 4.5 mmol) was dissolved in acetonitrile. Dimethylsulfide (6.6 mL) and acetic acid (2 mL)

were added and the resulting mixture cooled to 0–5° C. (ice bath) under nitrogen. Benzoyl peroxide (6.36 g, 26 mmol) was added in several portions over 5 hours, then stirred for an additional 10 minutes, and then the reaction mixture was poured into a mixture of ethyl acetate and saturated aq. sodium bicarbonate (100 mL each). The organic phase was separated, rinsed with water, brine (×2), and concentrated in vacuo to give a gum. This gum upon addition of 50 mL of diethyl ether afforded 1.56 g (70%) of an off a white crystalline solid. m.p.=159–160° C. Spectral data were consistent with the title compound.

General Preparation of Alkoxymethyl Halides

Bromomethyl methyl ether, chloromethyl methyl ether, 2-methoxyethoxymethyl chloride, 2-(trimethylsilyl) ethoxymethyl chloride, benzyl chloromethyl ether, 2-chloroethyl chloromethyl ether, chloromethyl methyl sulfide, and chloromethyl phenyl sulfide were purchased from commercial sources and used directly.

The methylthiomethyl ethers of 1-methoxy-2-propanol, 2-chloroethanol and 3-hydroxypropionitrile were prepared according to the procedure of J. C. Medina, et al. *Tetrahedron Lett.* 1988, 29, 3773 (Reagents a, Scheme 1). The methylthiomethyl ether of propanol and phenylthiomethyl ethers of 2-propanol and 2-methyl-1-propanol were prepared according to the procedure of E. J. Corey and M. G. Bock, *Tetrahedron Lett.* 1975, 3269 (Reagents b, Scheme 1). The methylthiomethyl ether of t-butyl alcohol was prepared in accordance with the method of J. H. Jones, *Syn. Commun.* 1986, 16, 1607 (Reagents c, Scheme 1).

Scheme 1

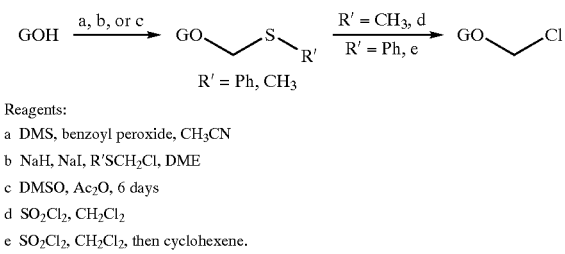

Reagents:
a DMS, benzoyl peroxide, CH$_3$CN
b NaH, NaI, R′SCH$_2$Cl, DME
c DMSO, Ac$_2$O, 6 days
d SO$_2$Cl$_2$, CH$_2$Cl$_2$
e SO$_2$Cl$_2$, CH$_2$Cl$_2$, then cyclohexene.

The aforementioned methylthiomethyl ethers were transformed to the corresponding chloromethyl ethers using the procedure of J. H. Jones, *Syn. Commun.* 1986, 16, 1607 while the phenylthiomethyl ethers were converted to the corresponding chloromethyl ethers by the method of T. Benneche, et al. *Acta Chemica Scandinavica* 1989, 74 (Reagents d, e Scheme 1). 2-(Chloromethoxy)ethyl acetate was prepared via the method of W. O. Foye, et al. *J. Het. Chem.* 1982, 19, 497.

General Preparation of Alkoxymethyl Ethers of 1a and 2a–g

A stirred mixture of 1a or 2a–g (1 eq), tetrabutylammonium iodide (0.3 eq) and diisopropylethylamine (3 eq) in methylene chloride (sufficient to make a 0.2 M solution of 1a or 2a–g in CH$_2$Cl$_2$) was treated with the appropriate bromo- or chloromethyl ether (2 eq). The resulting mixture was stirred for 16 hr, diluted with water, extracted with methylene chloride and the organic layer concentrated in vacuo. The crude residue was purified via silica gel chromatography to give the corresponding alkoxymethyl ether of 1a, 2a–2g. $^1$H-NMR and MS data were consistent for the desired products.

General Preparation of Alkyl and Arylthiomethyl Ethers of 1a

To a stirred solution of the desired chloromethyl sulfide (1.3 eq) in acetone (sufficient to make a 0.5 M solution of 1a in acetone) was added NaI (1.3 eq). After 16 hours 1a (1.0 eq) and powdered K$_2$CO$_3$ (2.5 eq) were added sequentially. After 1 hr the mixture was diluted with H$_2$O and extracted with ethyl acetate. The combined organic layers were dried (MgSO$_4$) and concentrated in vacuo. The crude residue was purified via silica gel chromatography to give the corresponding thiomethyl ether of 1a. $^1$H-NMR and MS data were consistent for the desired products.

General Preparation of Halomethyl Esters

Bromomethyl acetate, chloromethyl butyrate and chloromethyl pivalate were purchased from commercial sources and used directly. 1-Chloroethyl acetate was prepared according to the procedure of R. P. Iyer, *Syn. Commun.* 1995, 25, 2739. The remaining chloromethyl esters were prepared in accordance with the method of T. Benneche, et al. *Acta Chemica Scandinavica* 1989, 74 (Scheme 2).

Scheme 2

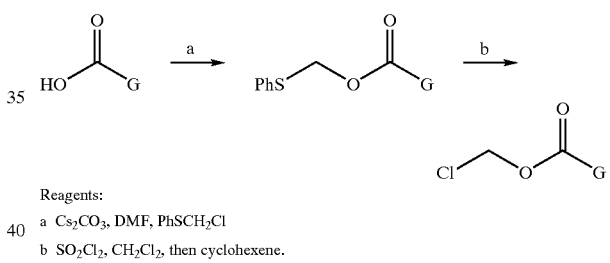

Reagents:
a Cs$_2$CO$_3$, DMF, PhSCH$_2$Cl
b SO$_2$Cl$_2$, CH$_2$Cl$_2$, then cyclohexene.

Alternatively, bromomethyl esters were prepared via a two step process outlined in Scheme 3. The methylene diacylates were formed under phase-transfer conditions. Cleavage of the resulting acylals was achieved using a modification of a known procedure by G. Grynkiewicz and R. Y. Tsien, *Pol. J. Chem.* 1987, 61, 443.

Scheme 3

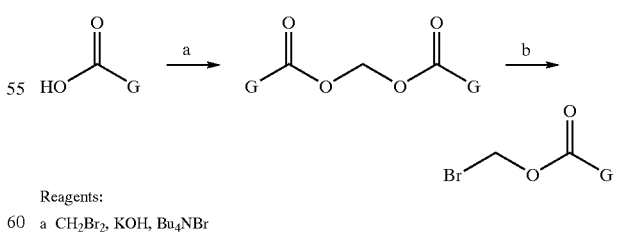

Reagents:
a CH$_2$Br$_2$, KOH, Bu$_4$NBr
b TMSBr (neat), ZnBr$_2$

General Preparation of Bromomethyl Esters

Potassium hydroxide (1.2 eq) was added to a solution of the desired acid (1.0 eq) in CH$_2$Br$_2$ (sufficient to make a 0.5–1.0 M solution of acid in $CH_2Br_2$) followed by tetrabutylammonium bromide (0.01 eq) and the mixture was stirred vigorously at 85° C. overnight. Upon cooling, the mixture was concentrated in vacuo and diluted with $Et_2O$. The precipitates were filtered off and the supernatant concentrated in vacuo to give a clear, colorless oil. $^1$H-NMR and GC-MS data were consistent with the desired product and the product could be taken to the next step without further purification.

Bromotrimethylsilane (1.5 eq) was added to a suspension of methylene diacylate (1.0 eq) and zinc bromide (0.2 eq). The reaction was monitored by $^1$H-NMR and after 23–48 hr, the mixture was cooled to 0° C. and diluted with EtOAc. Saturated aqueous sodium bicarbonate was added until evolution of gas ceased. The layers were separated and the organic layer was washed with sat. aq. $NaHCO_3$, dried ($MgSO_4$) and concentrated in vacuo. The resulting light, yellow oil could be used directly or distilled under vacuum to give a clear, colorless oil. $^1$H-NMR data was consistent with the desired product.

General Preparation of Alkyl Chloromethyl Carbonates (eq 2)

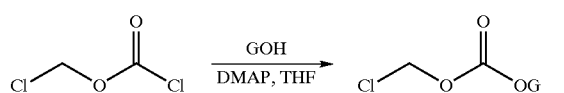

(eq 2)

A solution of 4-N,N-dimethylaminopyridine (DMAP) (2.81 g, 23 mmol) in THF (30 mL) was added slowly dropwise to a rapidly stirred solution of desired alcohol (23 mmol) and chloromethyl chloroformate (2.05 mL, 23 mmol) in THF (90 mL). After 2 hr most of the THF was removed in vacuo and the remaining residue diluted with $Et_2O$ (150 mL). The cloudy suspension was filtered, dried ($MgSO_4$) and concentrated in vacuo to give a light yellow liquid which was used without further purification. $^1$H-NMR data was consistent for each desired product.

General Preparation of Acyloxymethyl Ethers of 1a and 2a–g

Method A (Chloromethyl Esters and Carbonates)

Sodium iodide (1.3 eq) was added to a stirred solution of the desired chloromethyl esters (1.3 eq) in acetone (sufficient to make a 0.2 M solution of 1a or 2a–g in acetone). After stirring for 16 hours at ambient temperature, 1a or 2a–g (1 eq) and $K_2CO_3$ (2.4 eq) were added and stirring continued for 24 hours. The resulting mixture was diluted with water, extracted with EtOAc and the organic layer concentrated in vacuo. The crude residue was purified via silica gel chromatography to give the corresponding acyloxymethyl ether of 1a, 2a–g. $^1$H-NMR and MS data were consistent with the desired products.

Method B (Bromomethyl Esters)

Sodium iodide (0.5 eq), $K_2CO_3$ (1.5 eq), and the desired bromomethyl ester (1.2 eq) were added sequentially to a stirred solution of 1a or 2a–g (1.0 eq) in acetone (sufficient to make a 0.2 M solution of 1a or 2a–g in acetone). After stirring for 1–6 hours at ambient temperature, the resulting mixture was diluted with water and extracted with EtOAc. The organic layer was concentrated in vacuo and the crude residue was purified via silica gel chromatography (acetone/hexane as the eluant) to give the corresponding acyloxymethyl ether of 1a, 2a–g. $^1$H-NMR and MS data were consistent with the desired products.

Table One illustrates additional compounds of Formula One made from appropriate starting materials by the above described procedures. $^1$H-NMR spectral data for all of these compounds were consistent with the assigned structures.

TABLE ONE

| ## | Molecular Structure | AP | MI | m.p. |
|---|---|---|---|---|
| 4 | 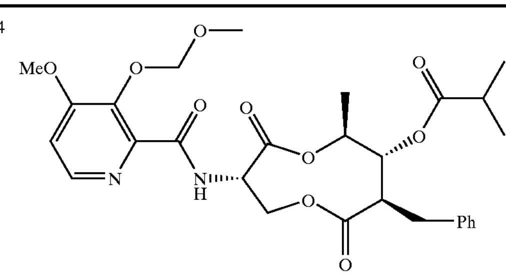 | White solid | 558 | 146–147 |
| 5 | 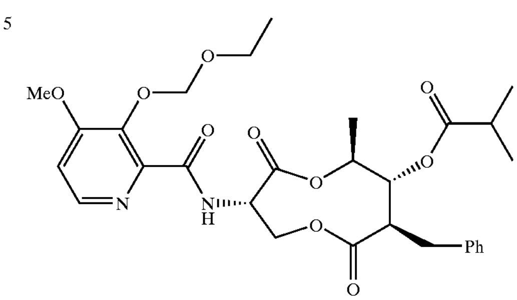 | White solid | 572 | 60–62 |

TABLE ONE-continued

| ## | Molecular Structure | AP | MI | m.p. |
|---|---|---|---|---|
| 6 | 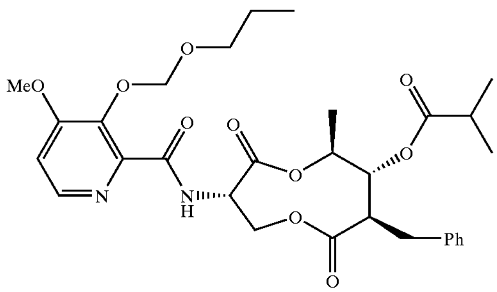 | Brown solid | 586 | |
| 7 | 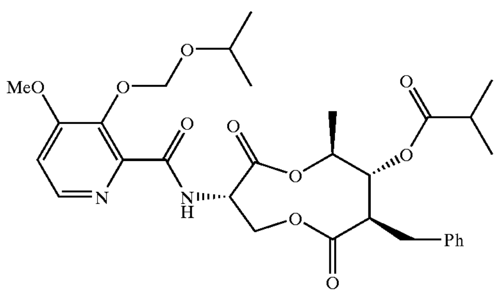 | White solid | M + 1 587 | 124–127 |
| 8 | 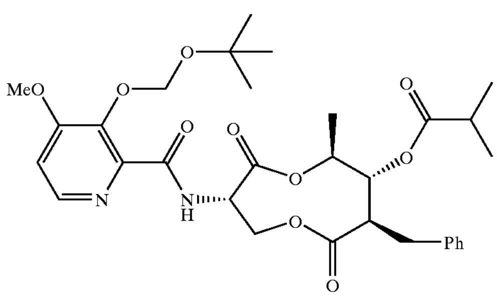 | White solid | M + 1 601 | |
| 9 | 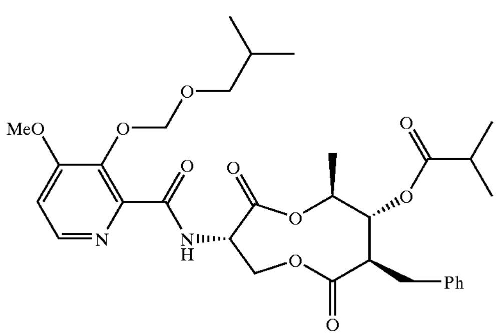 | White solid | 600 | 133–136 |
| 10 | 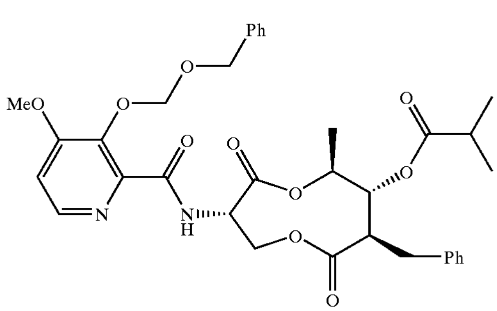 | White solid | M + 1 635 | 56–60 |

TABLE ONE-continued

| ## | Molecular Structure | AP | MI | m.p. |
|---|---|---|---|---|
| 11 | 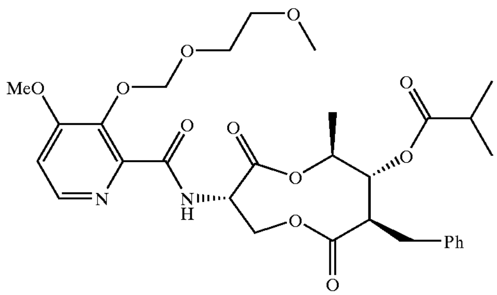 | Clear oil | 602 | |
| 12 | 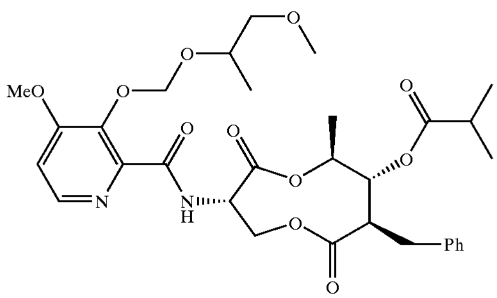 | White solid | 616 | |
| 13 | 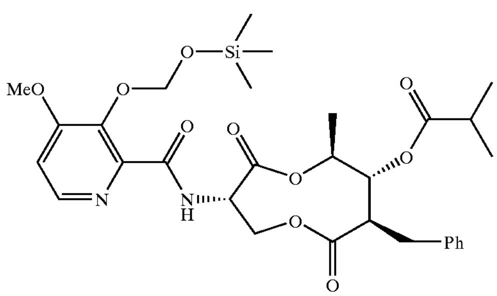 | White solid | | 50–52 |
| 14 | 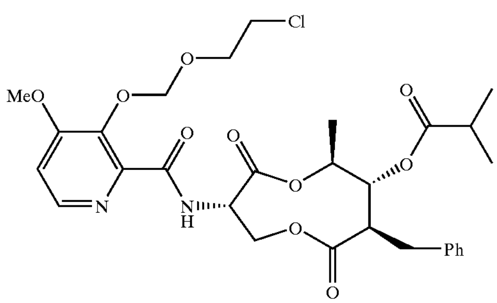 | White solid | 606 | 140–143 |
| 15 | 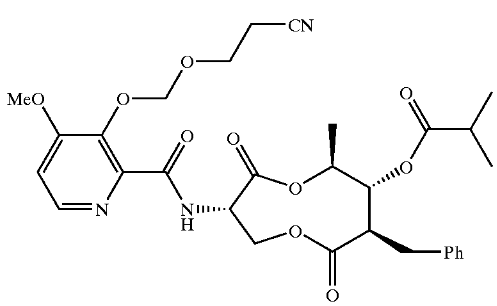 | White solid | 598 | 62–67 |

TABLE ONE-continued

| ## | Molecular Structure | AP | MI | m.p. |
|---|---|---|---|---|
| 16 | 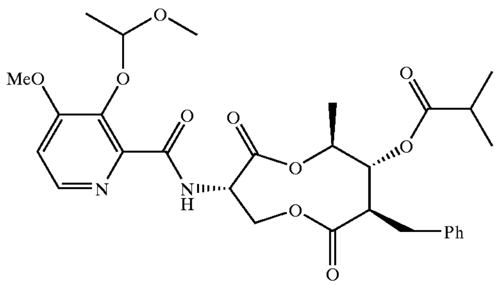 | White solid | M + 1 573 | |
| 17 | 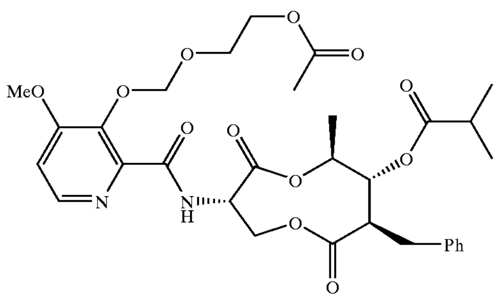 | White solid | M + 1 631 | |
| 18 | 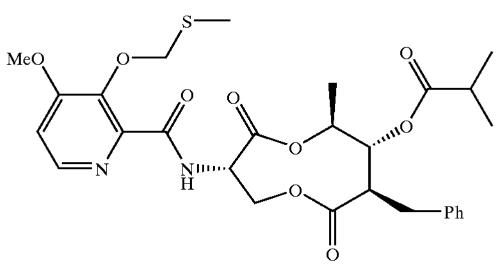 | White solid | M + 1 575 | 146–148 |
| 19 | 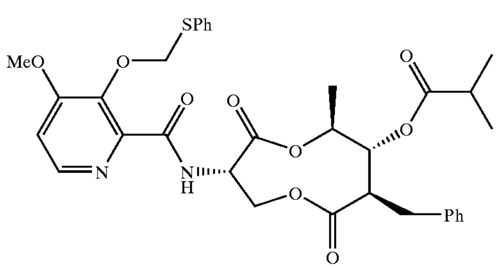 | White solid | M + 1 637 | 133–135 |
| 20 | 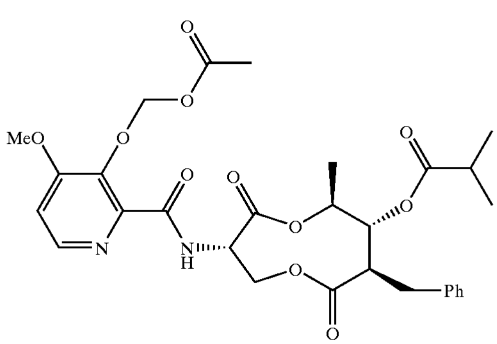 | White solid | M + 1 587 | 146–147 |

TABLE ONE-continued

| ## | Molecular Structure | AP | MI | m.p. |
|---|---|---|---|---|
| 21 | 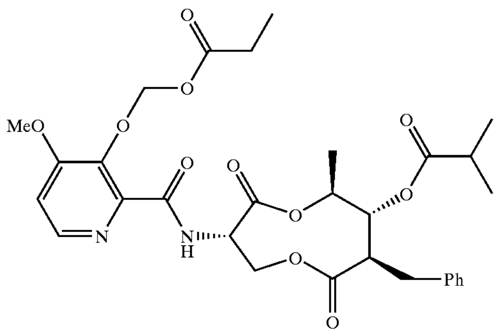 | White solid | M + 1 601 | |
| 22 | 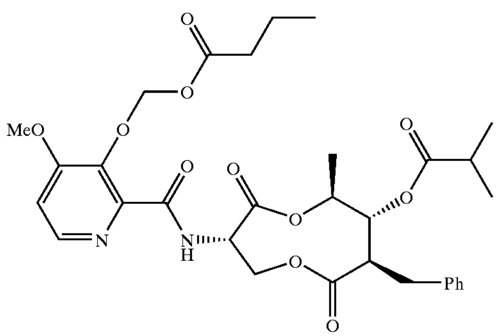 | White solid | 628 | 102–105 |
| 23 | 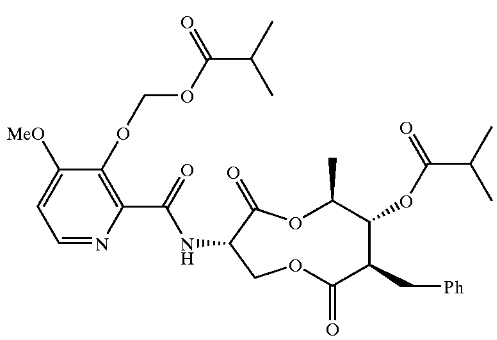 | White solid | M − 1 613 | 152–154 |
| 24 | 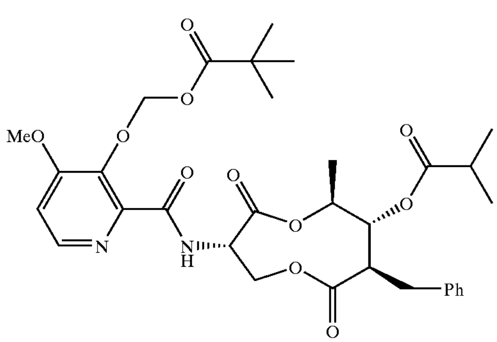 | White solid | M + 1 629 | 178–179 |

TABLE ONE-continued
| ## | Molecular Structure | AP | MI | m.p. |
|---|---|---|---|---|
| 25 | 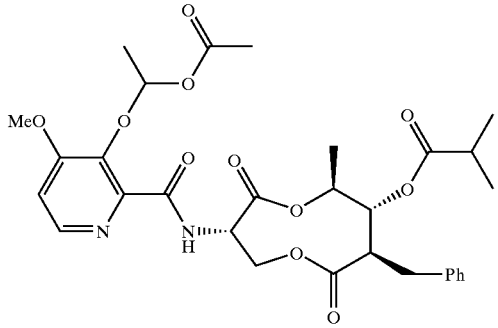 | White solid | M + 1 601 | 58–65 |
| 26 | 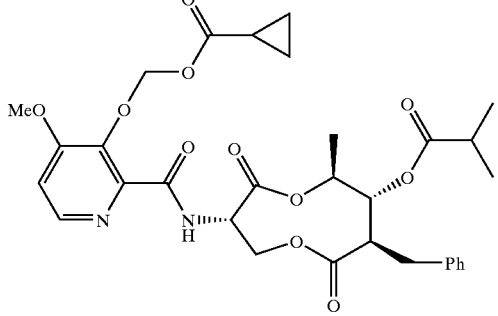 | White solid | M + 1 613 | 152–153 |
| 27 | 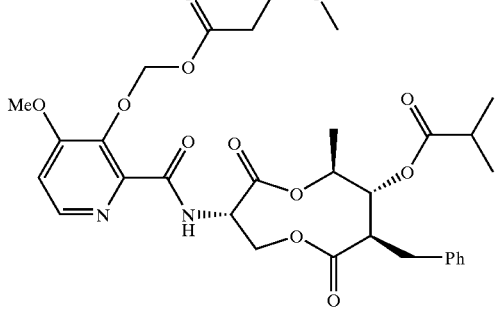 | White solid | M + 1 631 | 84–86 |
| 28 | 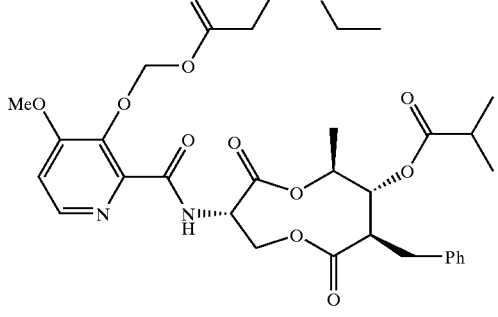 | White solid | M + 1 645 | 50–55 |

TABLE ONE-continued

| ## | Molecular Structure | AP | MI | m.p. |
|---|---|---|---|---|
| 29 | 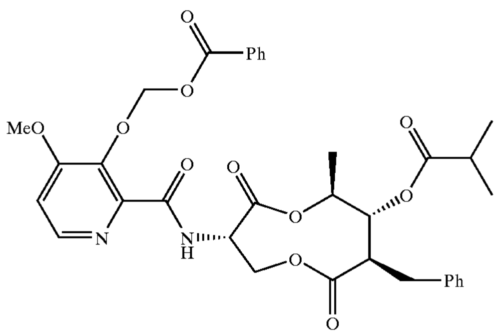 | White solid | M + 1 649 | 65–70 |
| 30 | 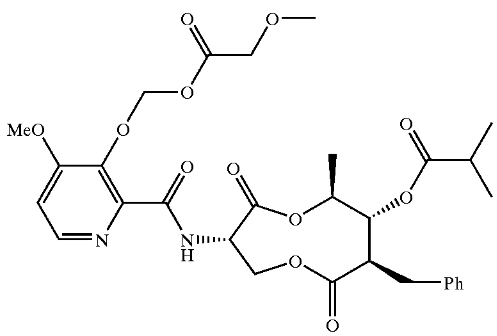 | White solid | M + 1 617 | |
| 31 | 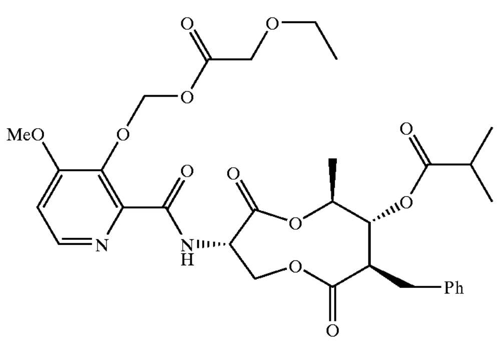 | White solid | M + 1 631 | 79–81 |
| 32 | 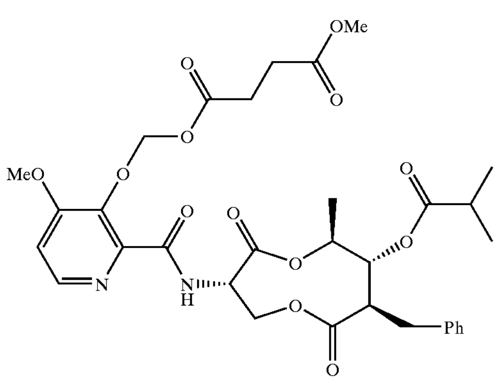 | White solid | M + 1 659 | |

TABLE ONE-continued
| ## | Molecular Structure | AP | MI | m.p. |
|---|---|---|---|---|
| 33 | 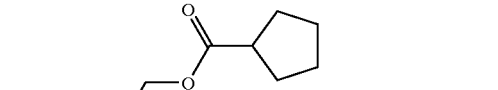 | White solid | M + 1 641 | 128–129 |
| 34 | 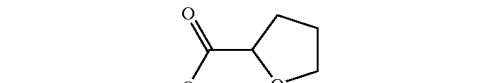 | White solid | M + 1 643 | |
| 35 | 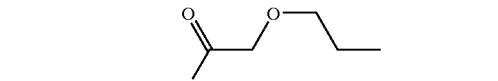 | White solid | M + 1 645 | |
| 36 | 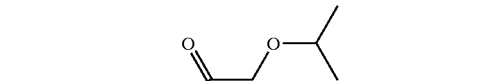 | White solid | M + 1 645 | |

TABLE ONE-continued

| ## | Molecular Structure | AP | MI | m.p. |
|---|---|---|---|---|
| 37 | 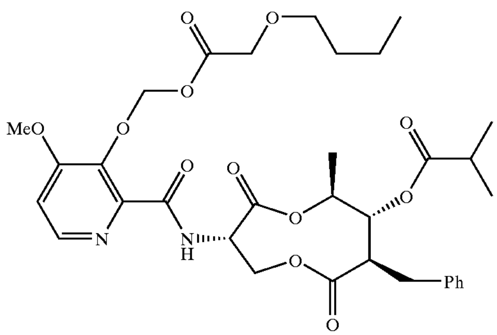 | White solid | M + 1 659 | |
| 38 | 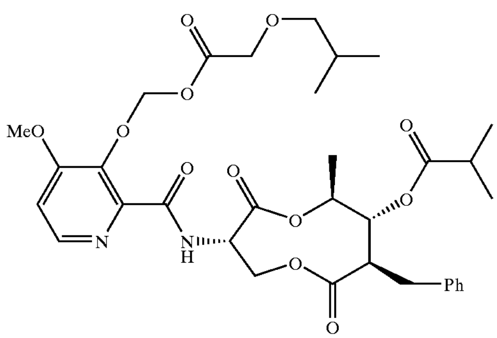 | White solid | M + 1 659 | |
| 39 | 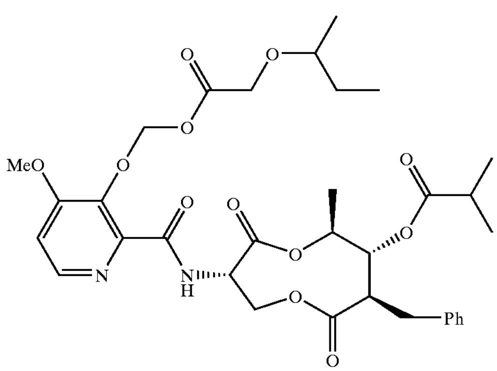 | White solid | M + 1 659 | |
| 40 | 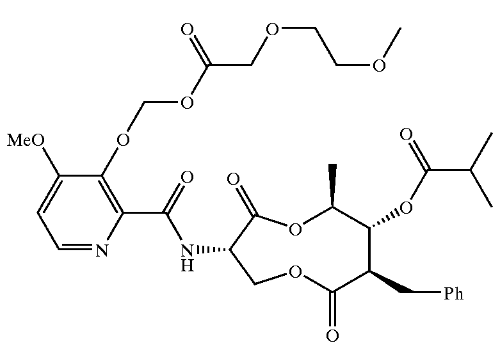 | Thick oil | M + 1 661 | |

TABLE ONE-continued
| ## | Molecular Structure | AP | MI | m.p. |
|---|---|---|---|---|
| 41 | 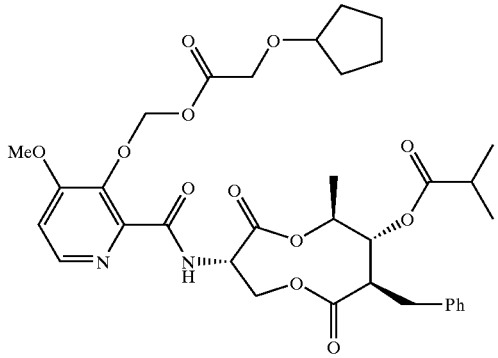 | White solid | M + 1 671 | |
| 42 | 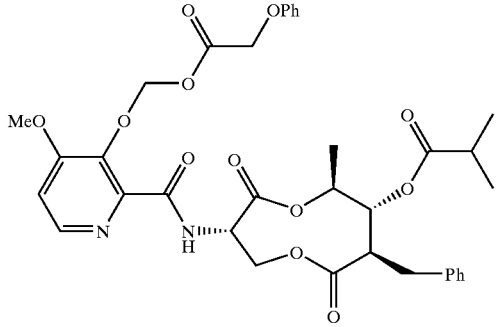 | White solid | M + 1 679 | |
| 43 | 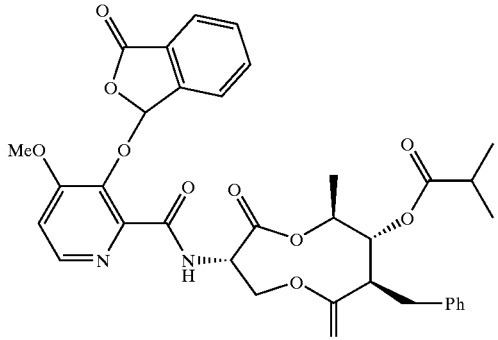 | White solid | M + 1 647 | |
| 44 | 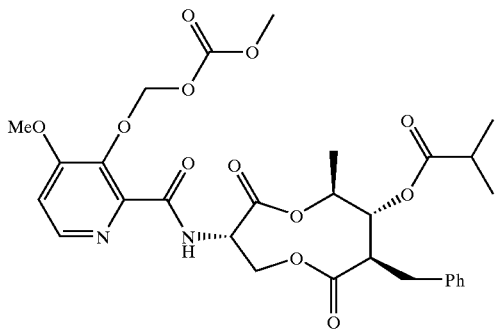 | White solid | 602 | 140–144 |

TABLE ONE-continued

| ## | Molecular Structure | AP | MI | m.p. |
|---|---|---|---|---|
| 45 | 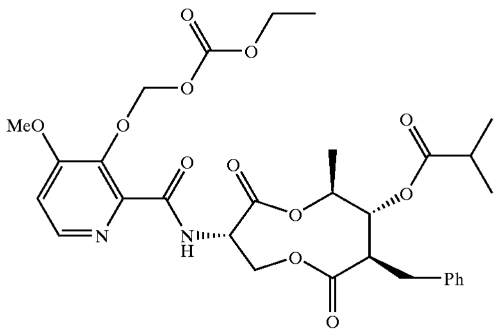 | White solid | 616 | |
| 46 | 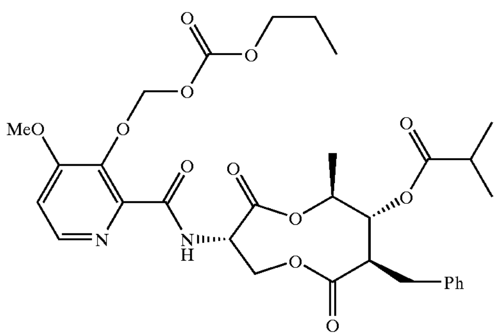 | White solid | 630 | |
| 47 | 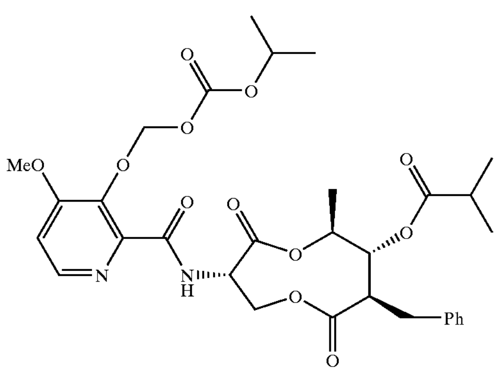 | Thick oil | M + 1 631 | |
| 48 | 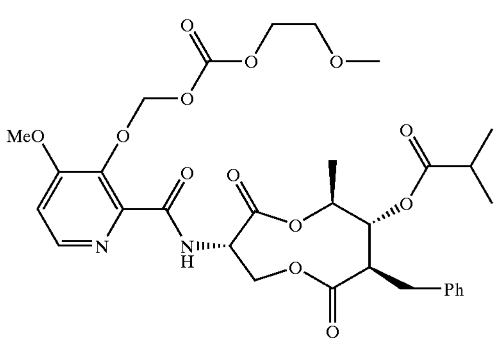 | White solid | M + 1 647 | |

TABLE ONE-continued

| ## | Molecular Structure | AP | MI | m.p. |
|---|---|---|---|---|
| 49 | 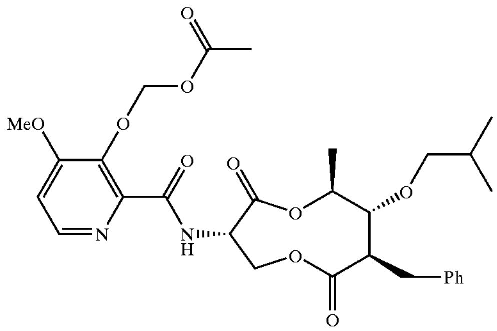 | White solid | | 130–131 |
| 50 | 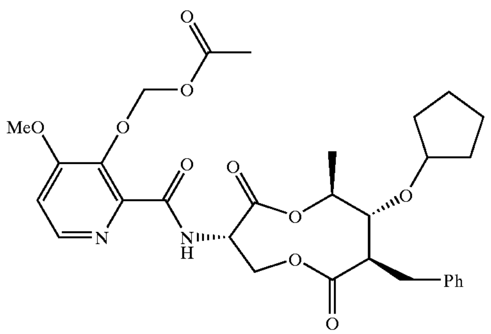 | White solid | M + 1 585 | 130–132 |
| 51 | 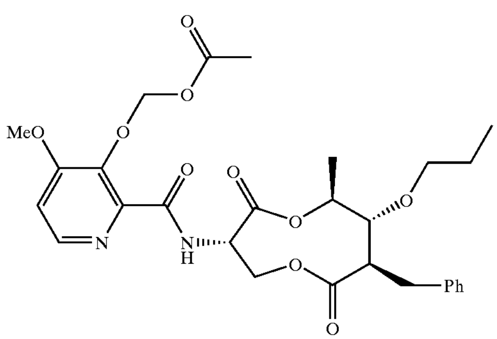 | White solid | M + 1 559 | 65–120 |
| 52 | 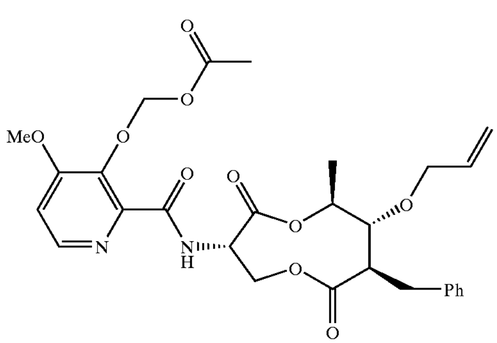 | White foam | M + 1 557 | |

TABLE ONE-continued

| ## | Molecular Structure | AP | MI | m.p. |
|---|---|---|---|---|
| 53 | (structure) | White foam | | 102–104 |
| 54 | (structure) | Yellow oil | M + 1 617 | |
| 55 | (structure) | Orange oil | M + 1 603 | |
| 56 | (structure) | Yellow oil | M + 1 599 | |

TABLE ONE-continued

| ## | Molecular Structure | AP | MI | m.p. |
|----|---------------------|-----|-----|------|
| 57 | 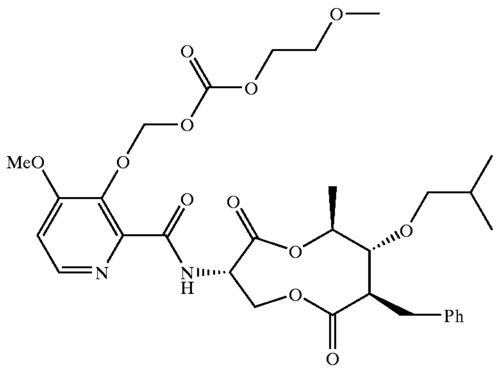 | Orange oil | M + 1 633 | |
| 58 | 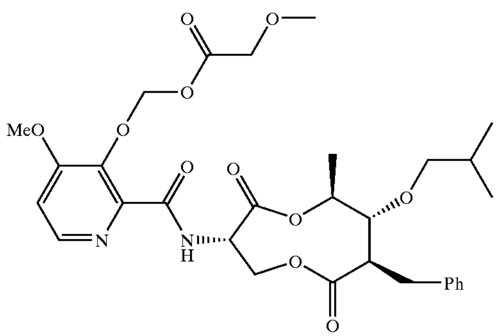 | Orange oil | M + 1 603 | |
| 59 | 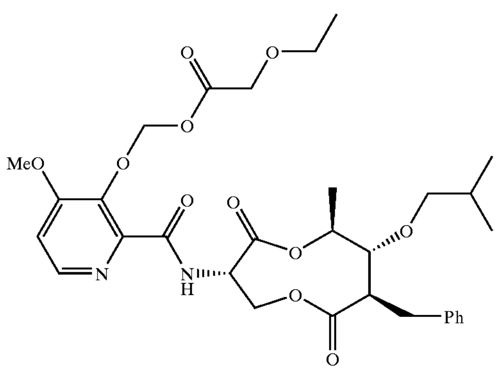 | Orange oil | M + 1 617 | |
| 60 | 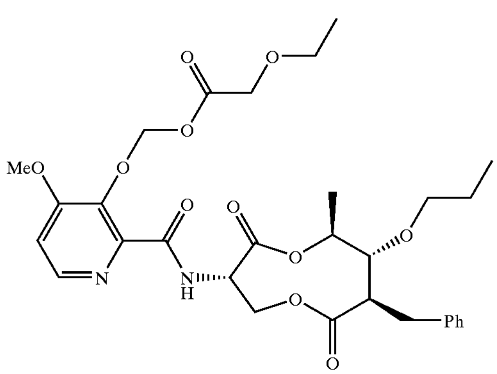 | Yellow oil | M + 1 603 | |

TABLE ONE-continued

| ## | Molecular Structure | AP | MI | m.p. |
|---|---|---|---|---|
| 61 | 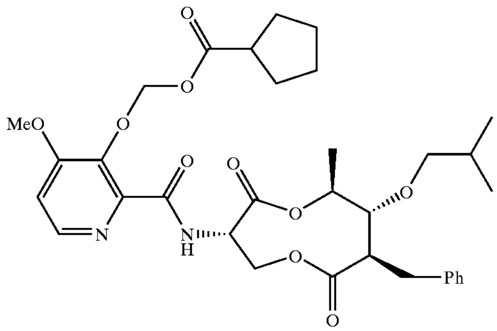 | Orange oil | M + 1 627 | |
| 62 | 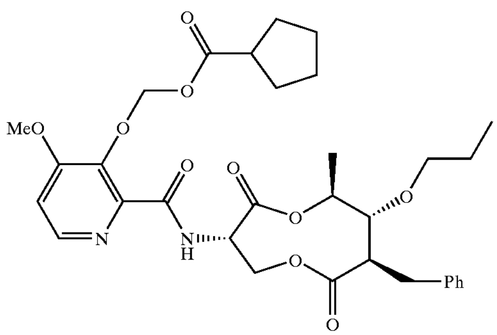 | Orange oil | M + 1 613 | |
| 63 | 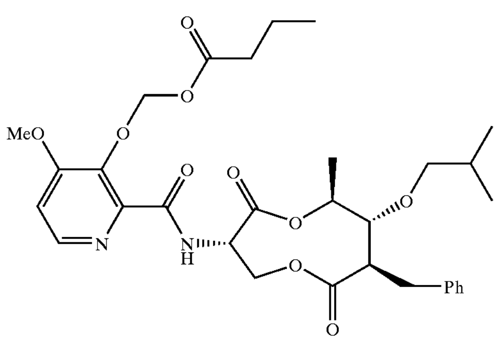 | Orange oil | M + 1 601 | |
| 64 | 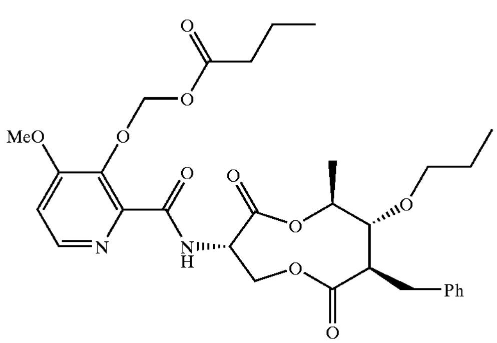 | Orange oil | M + 1 587 | |

TABLE ONE-continued
| ## | Molecular Structure | AP | MI | m.p. |
|---|---|---|---|---|
| 65 | 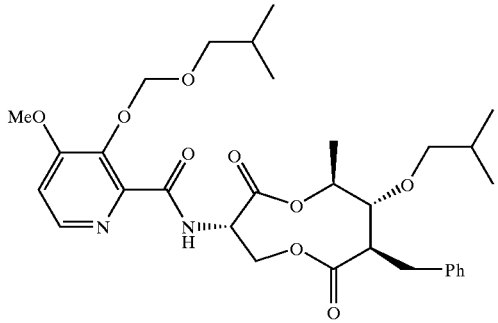 | Clear oil | M + 1 587 | |
| 66 | 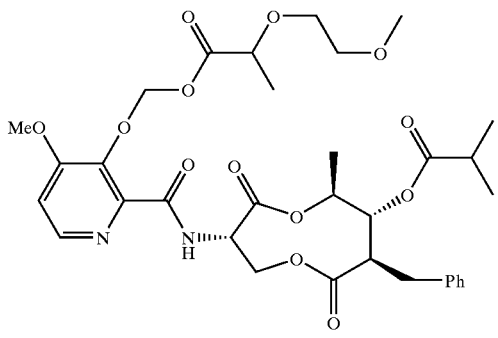 | White solid | M + 1 675 | |
| 67 | 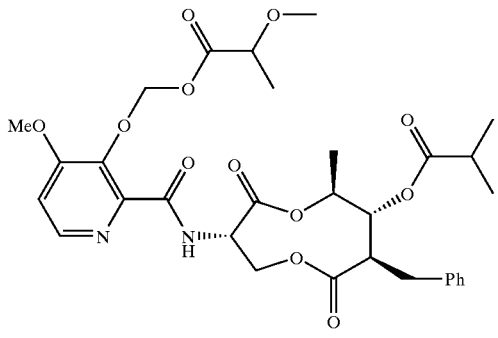 | White solid | M + 1 631 | |
| 68 | 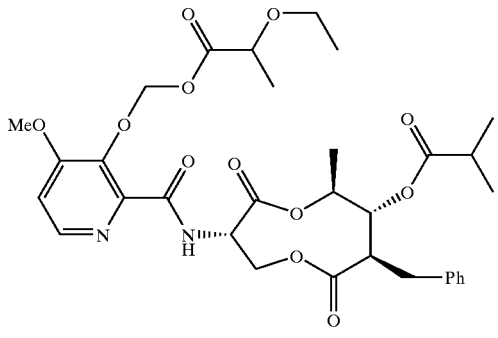 | White solid | M + 1 645 | |

TABLE ONE-continued

| ## | Molecular Structure | AP | MI | m.p. |
|---|---|---|---|---|
| 69 | 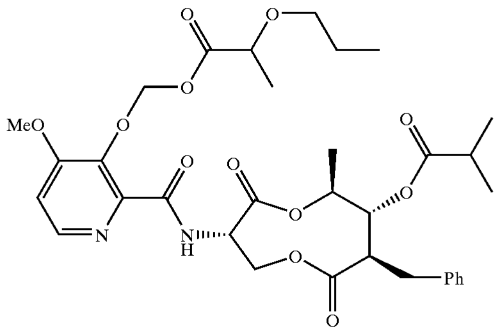 | White solid | M + 1 659 | |
| 70 | 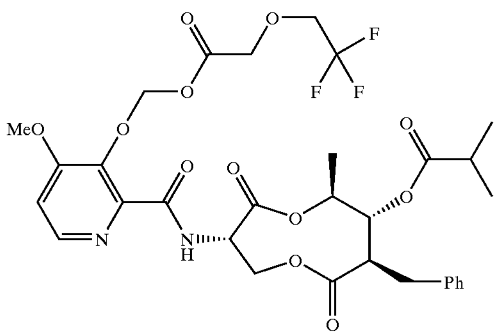 | White solid | M + 1 685 | |
| 71 | 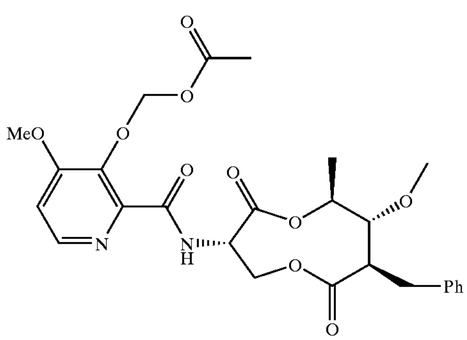 | White solid | M + 1 531 | |
| 72 | 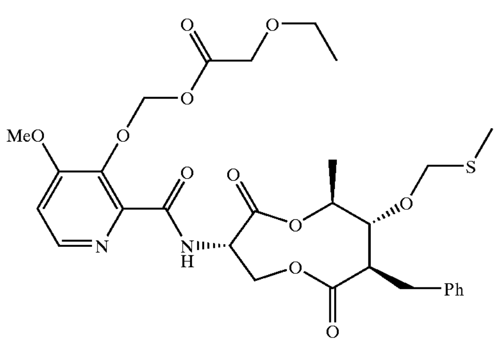 | Yellow oil | M + 1 621 | |

TABLE ONE-continued

| ## | Molecular Structure | AP | MI | m.p. |
|---|---|---|---|---|
| 73 | 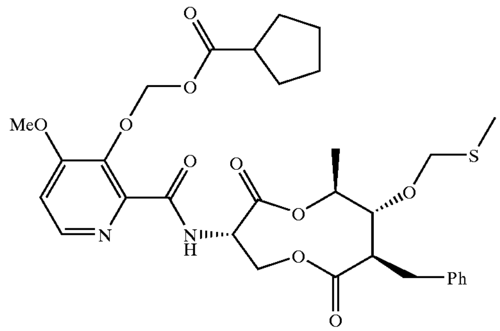 | Yellow oil | M + 1 631 | |
| 74 | 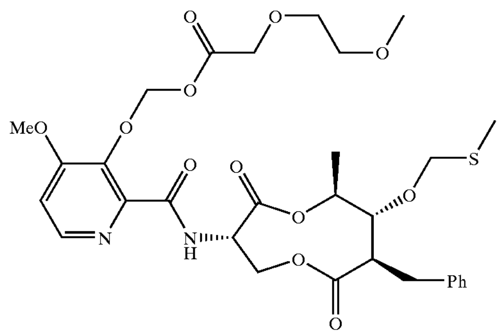 | Orange oil | M + 1 651 | |
| 75 | 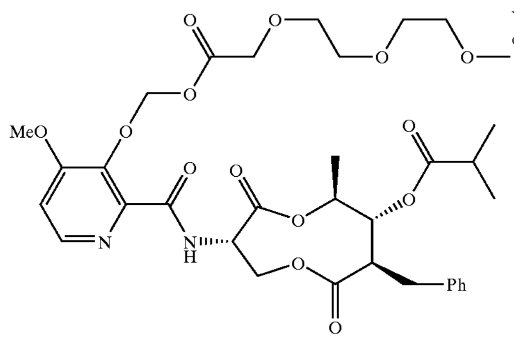 | Yellow oil | M + 1 705 | |

Table One Legend
## is the Compound Number.
AP is the Appearance.
MI is the Molecular Ion.
m.p. is as define earlier.

Biological Evaluation of Inhibition of In Vitro Fungal Growth

Culture Conditions: Suspensions of fungal conidia or mycelial fragments are prepared in sterile potato dextrose broth for *Magnaporthe grisea* (*Pyricularia oryzae*—PYRIOR), *Rhizoctonia solani* (RHIZSO), *Mycosphaerella graminicola* (*Septoria tritici*—SEPTTR), *Stagonospora nodorum* (*Leptosphaeria nodorum*—LEPTNO), *Ustilago maydis* (USTIMA), and in rye seed broth for *Phytophthora infestans* (PHYTIN). The suspensions are pipetted into sterile 96 well microtiter plates containing samples of the inventive compounds dissolved in dimethylsulfoxide. The concentration of the inventive compounds varies from 0.001 to 100 ppm with the final solvent concentration not exceeding 1% of the medium. The fungi are allowed to grow for various time intervals at 24 to 30° C. until the wells become turbid from the growth of the fungi in control wells containing only the solvent. At that time growth inhibition is determined by visual inspection of each well and the percent inhibition of growth as compared to the solvent treated controls is determined.

Biological Evaluation of Control of In Vitro Whole Plant Fungal Infection

Compound formulation was accomplished by dissolving technical materials in acetone, with serial dilutions then made in acetone to obtain desired concentrations. Final treatment volumes were obtained by adding 9 volumes 0.01% Triton X-100.

Downy Mildew of Grape (*Plasmopara viticola*—PLASVI) (24 Hour Protectant): Vines (cultivar Carignane) were grown from seed in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous sporangia suspension of *Plasmopara viticola*, and kept in a dew chamber overnight. The plants were then transferred to the greenhouse until disease developed on the untreated control plants.

Late Blight of Tomato (*Phytophthora infestans*—PHYTIN) (24 Hour Protectant): Tomatoes (cultivar Rutgers) were grown from seed in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous sporangia suspension of *Phytophthora infestans*, and kept in a dew chamber overnight. The plants were then transferred to the greenhouse until disease developed on the untreated control plants.

Brown Rust of Wheat (*Puccinia recondita*—PUCCRT) (24 Hour Protectant): Wheat (cultivar Yuma) was grown in a soilless peat-based potting mixture ("Metromix") and mineral soil (50/50 mix) until the seedlings were 10–20 cm tall. These plants were then sprayed to run-off with the test compound at a rate of 100 ppm. After 24 hours the test plants were inoculated by spraying with an aqueous spore suspension of *Puccinia_recondita*, and kept in a dew chamber overnight. The plants were then transferred to the greenhouse until disease developed on the untreated control plants.

Powdery Mildew of Wheat (*Erysiphe graminis*—ERYSGT) (24 Hour Protectant): Wheat (cultivar Monon) was grown in a soilless peat-based potting mixture ("Metromix") and mineral soil (50/50 mix) until the seedlings were 10–20 cm tall. These plants were then sprayed to run-off with the test compound at a rate of 100 ppm. After 24 hours the test plants were inoculated by dusting with conidia from powdery mildew infected wheat plants. The plants were then transferred to the greenhouse until disease developed on the untreated control plants.

Leaf Blotch of Wheat (*Septoria tritici*—SEPTTR) (24 Hour Protectant): Wheat (cultivar Monon) was grown in a soilless peat-based potting mixture ("Metromix") and mineral soil (50/50 mix) until the seedlings were 10–20 cm tall. These plants were then sprayed to run-off with the test compound at a rate of 100 ppm. After 24 hours the test plants were inoculated by spraying with an aqueous spore suspension of *Septoria tritici*, and kept in a dew chamber overnight. The plants were then transferred to the greenhouse until disease developed on the untreated control plants.

Glume Blotch of Wheat (*Leptosphaeria nodorum*—LEPTNO) (24 Hour Protectant): Wheat (cultivar Yuma) was grown in a soilless peat-based potting mixture ("Metromix") and mineral soil (50/50 mix) until the seedlings were 10–20 cm tall. These plants were then sprayed to run-off with the test compound at a rate of 100 ppm. After 24 hours the test plants were inoculated by spraying with an aqueous spore suspension of *Leptosphaeria nodorum*, and kept in a dew chamber overnight. The plants were then transferred to the greenhouse until disease developed on the untreated control plants.

In Table Two, tests T1–T6, a "++" indicates that the test material gave at least 75–100% control of fungal infection when compared to disease incidence on untreated plants, a "+" indicates that the test material gave 25–74% control of fungal infection, and a "−" indicates <25% control of fungal infection of the designated pathogen at a concentration of 100 ppm. A blank space indicates not tested.

In Table Two, tests T7–T12, a "+" indicates that the test material gave at least 80% growth inhibition and a "−" indicates less than 80% growth inhibition of the designated pathogen when incorporated into the growth medium at a concentration of 25 ppm. A blank space indicates not tested.

TABLE TWO

| ## | T1 | T2 | T3 | T4 | T5 | T6 | T7 | T8 | T9 | T10 | T11 | T12 |
|---|---|---|---|---|---|---|---|---|---|---|---|---|
| 4 | + | ++ | − | − | ++ |    | + | − | + | − | − | − |
| 5 | + | ++ | − | − | ++ | ++ | + | − | − | − | − | − |
| 6 | + | ++ | − | − | ++ |    | + | − | − | − | − | − |
| 7 | + | ++ | − | + | ++ | ++ | + | − | − | − | − | + |
| 8 | − | ++ | − | − | ++ | ++ | + | − | − | − | − | + |
| 9 | − | ++ | − | − | ++ | +  | + | − | − | + | + | + |
| 10 | − | ++ | − | + | ++ |    | + | + | − | − | + | − |
| 11 | + | ++ | − | − | ++ |    |   |   |   |   |   |   |
| 12 | + | ++ | − | ++ | ++ | ++ | + | − | + | + | + | + |
| 13 | − | ++ | − | + | ++ | ++ | + | − | − | + | − | − |
| 14 | − | ++ | − | − | ++ | ++ | + | − | − | − | − | − |
| 15 | − | ++ | − | − | ++ | ++ | + | − | − | + | − | + |
| 16 | − | ++ | − | − |    |    | + | − | + | − | + | − |
| 17 | − | ++ | − | + | ++ | ++ | + | − | − | + | + | − |
| 18 | − | ++ | − | + | ++ |    | + | − | + | + | + | − |
| 19 | − | ++ | − | − | ++ |    | + | − | + | + | + | − |
| 20 | ++ | ++ | − | − | ++ | ++ | + | − | − | − | − | + |
| 21 | + | ++ | − | + | ++ | ++ | + | − | + | − | + | − |
| 22 | ++ | ++ | − | − | ++ | ++ | + | − | − | − | − | − |
| 23 | + | ++ | − | ++ | ++ |    | + | − | − | − | − | + |
| 24 | + | ++ | − | − | ++ | ++ | − | − | + | − | + | − |
| 25 | − | ++ | − | + | ++ | ++ | + | − | − | − | + | + |
| 26 | + | ++ | − | − | ++ | ++ | + | − | − | − | − | − |
| 27 | ++ | ++ | − | + | ++ | ++ | + | − | + | − | + | − |
| 28 | + | ++ | − | + | ++ | ++ | + | − | + | + | + | + |
| 29 | + | ++ | − | + | ++ | ++ | + | − | − | − | − | − |
| 30 | ++ | ++ | − | + | ++ | ++ | + | − | + | + | − | + |
| 31 | + | ++ | − | ++ | ++ | ++ | + | − | + | − | − | − |
| 32 | + | ++ | − | ++ | ++ | ++ | + | − | + | − | − | − |
| 33 | + | ++ | − | + | ++ | ++ | + | − | + | − | − | − |
| 34 | + | ++ | − | − | ++ | ++ | + | − | − | − | − | − |
| 35 | + | ++ | − | + | ++ | ++ | + | − | + | + | + | − |
| 36 | − | ++ | − | − | ++ | ++ | + | − | + | − | + | − |
| 37 | + | ++ | − | − | ++ | ++ | + | − | + | − | + | + |
| 38 | + | ++ | − | − | ++ | ++ | + | − | + | − | + | − |
| 39 | + | ++ | − | − | ++ | ++ | + | − | + | − | + | − |
| 40 | + | ++ | − | + | ++ | ++ | + | − | + | + | + | + |
| 41 | + | ++ | − | + | ++ | ++ | + | − | + | − | + | + |
| 42 | − | ++ | − | − | ++ | −  | + | − | + | − | + | − |
| 43 | + | ++ | − | + | ++ | ++ | + | − | − | − | + | − |
| 44 | + | ++ | − | + | ++ | ++ | + | − | − | − | + | − |
| 45 | + | ++ | + | ++ | ++ | ++ | + | − | + | − | − | − |
| 46 | + | ++ | − | + | ++ | ++ | + | − | + | − | − | − |
| 47 | − | ++ | − | + | ++ |    |   |   |   |   |   |   |
| 48 | ++ | ++ | − | − | ++ | ++ | + | − | − | − | − | + |
| 49 | ++ | ++ | + | − | ++ | ++ | + | − | + | − | + | − |
| 50 | + | ++ | + | + | ++ | ++ | + | − | − | − | − | − |
| 51 | ++ | ++ | − | + | ++ |    | + | − | + | + | + | − |
| 52 | − | ++ | − | + | ++ |    | + | − | + | + | + | − |
| 53 | − | ++ | − | + | ++ |    | + | + | + | − | + | − |
| 54 | ++ | ++ | − | ++ | ++ | ++ | + | − | + | − | + | + |
| 55 | ++ | ++ | − | + | ++ | ++ | + | − | + | − | + | − |
| 56 | ++ | ++ | − | + | ++ | ++ | + | − | + | − | + | − |
| 57 | ++ | ++ | − | + | ++ | ++ | + | − | + | − | + | + |
| 58 | ++ | ++ | − | + | ++ | ++ | + | + | + | − | + | + |
| 59 | ++ | ++ | − | + | ++ | ++ | + | + | + | − | + | + |
| 60 | ++ | ++ | − | + | ++ | ++ | + | + | + | − | + | + |
| 61 | ++ | ++ | − | + | ++ | ++ | + | − | + | − | + | + |
| 62 | ++ | ++ | − | − | ++ | ++ | + | − | + | − | + | + |
| 63 | ++ | ++ | − | ++ | ++ | ++ | + | − | + | − | + | − |

TABLE TWO-continued

| ## | T1 | T2 | T3 | T4 | T5 | T6 | T7 | T8 | T9 | T10 | T11 | T12 |
|----|----|----|----|----|----|----|----|----|----|-----|-----|-----|
| 64 | ++ | ++ | −  | ++ | ++ | ++ | +  | −  | +  | −   | +   | −   |
| 65 | −  | ++ | −  | −  | ++ | ++ |    |    |    |     |     |     |
| 66 |    | ++ | −  | −  | ++ |    | −  | −  | −  | −   | −   | −   |
| 67 |    | ++ | −  | −  | ++ |    | −  | −  | −  | −   | −   | +   |
| 68 |    | ++ | −  | −  | ++ |    | +  | −  | −  | +   | +   | +   |
| 69 |    | ++ | −  | −  | ++ |    | +  | −  | +  | +   | +   | +   |
| 70 |    | ++ | −  | −  | ++ |    | +  | −  | −  | −   | −   | +   |
| 71 |    |    |    |    |    |    | +  | −  | +  | −   | +   | +   |
| 72 | +  | ++ | −  | −  | ++ | +  | +  | −  | +  | −   | +   | +   |
| 73 | +  | ++ | −  | −  | ++ | ++ | +  | −  | +  | −   | +   | +   |
| 74 | +  | ++ | −  | −  | ++ | +  | +  | −  | +  | −   | +   | +   |
| 75 | ++ |    | −  | +  |    |    | +  | −  | +  | −   | +   | +   |

Table Two Legend
## is the Compound Number.
T1 is ERYSGT in vivo 1 Day Protectant.
T2 LEPTNO in vivo 1 Day Protectant.
T3 PHYTIN in vivo 1 Day Protectant.
T4 PLASVI in vivo 1 Day Protectant.
T5 PUCCRT in vivo 1 Day Protectant.
T6 SEPTTR in vivo 1 Day Protectant.
T7 LEPTNO in vitro Growth Inhibition.
T8 PHYTIN in vitro Growth Inhibition.
T9 PYRIOR in vitro Growth Inhibition.
T10 RHIZSO in vitro Growth Inhibition.
T11 SEPTTR in vitro Growth Inhibition.
T12 USTIMA in vitro Growth Inhibition.

We claim:
1. A compound according to Formula One:

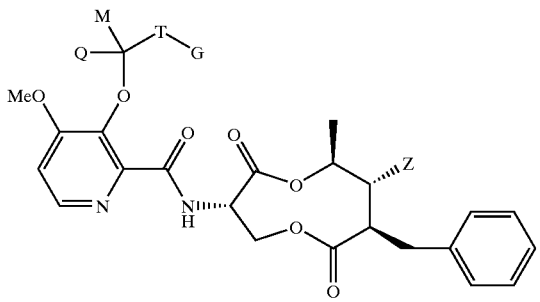

Formula One wherein:
Z is selected from the group consisting of H, $R^{11}$, $OR^{11}$, $OC(O)R^{11}$, $OC(O)OR^{11}$, and $OC(O)NR^{11}R^{12}$, $OC(O)NR^{11-12}R^{12-11}$;
$R^{11}$ is selected from the group consisting of $C_1$–$C_8$ alkyl, $C_2$–$C_8$ alkenyl, $C_2$–$C_8$ alkynyl, $C_3$–$C_8$ cycloalkyl, aryl, and heteroaryl;
$R^{12}$ is selected from the group consisting of H, $C_1$–$C_6$ alkyl, $C_3$–$C_6$ cycloalkyl, $C_2$–$C_5$ alkenyl, and $C_2$–$C_5$ alkynyl;
$NR^{11-12}R^{12-11}$ is a 5 to 8 membered ring, where the members of the ring are selected from the group consisting of C, O, and S
Q is selected from the group consisting of H, $CH_3$, $CH_2CH_3$, $CF_3$, Ph, $CH=CH_2$, and cyclopropyl;
M is selected from the group consisting of H, $CH_3$, $CH_2CH_3$, $CF_3$, Ph, $CH=CH_2$, or cyclopropyl;
T is selected from the group consisting of O, OC(O), OC(O)O, S, SC(O), SC(O)O,

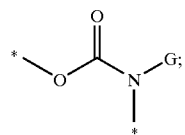

G is selected from the group consisting of H, $C_1$–$C_6$ alkyl, $C_2$–$C_6$ alkenyl, $C_2$–C6 alkynyl, $C_3$–$C_6$ cycloalkyl, aryl, and heteroaryl;
optionally, G and M may form a 3–8 membered carbocyclic system;
optionally, M and Q may form a 3–8 membered carbocyclic system;
wherein each of the alkyl, alkoxy, alkenyl, alkynyl, cycloalkyl, cycloalkenyl, benzyl, aryl, and heteroaryl may be substituted with one or more substituents.

2. A compound of claim 1 which is {[2-({[(3S,7R,8R,9S)-7-benzyl-8-(isobutyryloxy)-9-methyl-2,6-dioxo-1,5-dioxonan-3-yl]amino}carbonyl)-4-methoxy-3-pyridinyl]oxy}methyl cyclopentanecarboxylate.

3. A compound of claim 1 which is (3S,6S,7R,8R)-8-benzyl-3-{[(3-{[(ethoxyacetyl)oxy]methoxy}-4-methoxy-2-pyridinyl)carbonyl]amino}-6-methyl-4,9-dioxo-1,5-dioxonan-7-yl 2-methylpropanoate.

4. A composition comprising (1) a compound according to claim 1, 2, or 3, and (2) at least one compound selected from other fungicides, insecticides, nematocides, miticides, arthropodicides, or bactericides.

5. A process comprising using a compound according to claims 1, 2, or 3, or a composition according to claim 4, in a disease inhibiting and phytologically acceptable amount, to prevent, control, or eradicate, fungal disease.

* * * * *